(12) United States Patent
Li (10) Patent No.: US 8,252,340 B2
(45) Date of Patent: Aug. 28, 2012

(54) EXTRACT FOR TREATING THROMBOTIC DISEASES

(75) Inventor: Zhenguo Li, Mudanjiang (CN)

(73) Assignee: Mudanjiang Youbo Pharmaceutical Co., Ltd, Mudanjiang, Heilongjiang (CN)

( * ) Notice: Subject to any disclaimer, the term of this patent is extended or adjusted under 35 U.S.C. 154(b) by 1123 days.

(21) Appl. No.: 12/064,962

(22) PCT Filed: Jun. 26, 2007

(86) PCT No.: PCT/CN2007/070190
§ 371 (c)(1),
(2), (4) Date: Feb. 27, 2008

(87) PCT Pub. No.: WO2008/003259
PCT Pub. Date: Jan. 10, 2008

(65) Prior Publication Data
US 2008/0206352 A1     Aug. 28, 2008

(30) Foreign Application Priority Data
Jun. 28, 2006   (CN) .......................... 2006 1 086680

(51) Int. Cl.
*A61K 35/12* (2006.01)
*A61K 38/48* (2006.01)

(52) U.S. Cl. ..................................... 424/520; 424/94.64
(58) Field of Classification Search ....................... None
See application file for complete search history.

(56) References Cited

U.S. PATENT DOCUMENTS

| 4,668,662 A | * | 5/1987 | Tripier .......................... 514/14.9 |
| 5,137,590 A | * | 8/1992 | Villagrasa ..................... 156/62.4 |
| 8,012,430 B2 | * | 9/2011 | Yokoyama et al. ........... 422/503 |
| 2005/0032745 A1 | * | 2/2005 | Weitz et al. ..................... 514/56 |

FOREIGN PATENT DOCUMENTS

| CN | 03148281.3 | 2/2004 |
| CN | 200510000266.7 | 1/2005 |
| CN | 200410101538.8 | 8/2005 |

OTHER PUBLICATIONS

DERWENTCN1651079A, Aug. 10, 2005, Abstract in English Only provided.*

* cited by examiner

*Primary Examiner* — Debbie K Ware (57) ABSTRACT

An extract for preventing or treating thrombotic disease, particularly, an extract of leech and/or earthworm with molecular weight of not more than 5800 Dalton, and processes for preparation, pharmaceutical compositions and uses thereof. The extract of the present invention has improved significantly safety without any reducing in pharmaceutical activities or the therapeutical effects as compared to existing products.

4 Claims, 4 Drawing Sheets

EXTRACT FOR TREATING THROMBOTIC DISEASES

BACKGROUND OF THE PRESENT INVENTION

1. Field of Invention

The present invention relates to an extract for preventing or treating thrombotic diseases, and more particularly to an extract of leech and/or earthworm with molecular weight of less than 5,800 Dalton, and pharmaceutical composition, processes for preparation and use thereof.

2. Description of Related Arts

As a kind of classic drug of removing blood clot, the Chinese Pharmacopeia records three kinds of leech *Whitmania pigra* Whitman, *Hirudo nipponica* Whitman and *Whitmania ac-ranulata* Whitman. Among them, *Whitmania pigra* Whitman is the most widely-used for drug. The main ingredients of leech are protein, polypeptide, amino acids, nucleic acid, enzyme, sugars, trace elements and etc. The qualitation and quantitation researches about ingredients in leech have been reported for many times. The main methods are TLC, HPLC, and electrophoretic method. The main micromolecular ingredients in leech are hypoxanthine, xanthine, uracil, uracil riboside and etc. Both Pyrimidine and Purine are unsaturated heterocyclic compounds containing N atoms.

As Chinese traditional medicine, earthworm in the Chinese Pharmacopeia has effects of clearing away heat, calming, getting through arteries and veins, smoothing breathe and diuretic. There are four kinds of earthworm in the Chinese pharmacopeia. They are *Pheretima aspergillum* (E. Perrier), *Pheretima vulgaris* Chen, *Pheretima guillelmi* (Michaelsen) and *Pheretima pectinifera* Michaelsen. Among them, *Pheretima aspergillum* (E. Perrier) also known as *Lumbricus* is the most widely-used for drug. The main ingredients in earthworm are protein, amino acids, nucleic acid, enzyme, sugars and etc. The qualitation and quantitation researches about ingredients in earthworm have been reported. The main micromolecular ingredients in earthworm are hypoxanthine and compounds containing N atoms.

Extracts of leech and earthworm is the active components in Shuxuetong Injection which possesses high performance and immediate effect in treating cardiovascular and cerebrovascular diseases. Chinese patent applications 03148281.3, 200410101538.8 and 200510000266.7 disclose Shuxuetong Injection and processes for preparation thereof respectively. All content of the applications were referred in the present invention.

Materials possessing immunogenicity often are macromolecule, and the larger molecular weight, the better the immunogenicity. Polypeptides with micromolecule often have no or few immunogenicity. Antigens often are macromolecule because the following probably reasons: (1) The relative molecular weight of antigens are bigger, the superficial Specific chemical genes are more, so that the effect of stimulating immunologic cells is better and the immunologic response is stronger; (2) Macromolecular antigens having complex chemical compositions and stable structures can not be destroyed and eliminated easily and can stay in human being's bodies for long time. So they can stimulate immunologic system persistently and immunologic response emerges. Insulin human composed of 51 amino acids (standard molecular weight is 5800 Dalton) is the boundary of distinguishing high molecular weight materials with low molecular weight materials. The high molecular weight materials are controlled strictly in injection.

SUMMARY OF THE PRESENT INVENTION

A main object of the present invention is to provide an extract for preventing or treating thrombotic diseases, and more particularly to an extract of leech and/or earthworm with molecular weight of less than 5,800 Dalton, and processes for preparation and use thereof. Comparing with present technology, the extract is safer and more unsuspecting in clinic.

Accordingly, in order to accomplish the above object, the present invention is described as follow:

An extract for preventing or treating thrombotic diseases is characterized by molecular weight of less than 5,800 Dalton.

The extract is extract of leech, earthworm or mixture of the two. The extract mixture of leech and earthworm is the mixture of extract of leech and extract of earthworm, or extract of mixture of leech and earthworm.

The leech is *Whitmania pigra* Whitman, *Hirudo nipponica* Whitman or *Whitmania ac-ranulata* Whitman. The earthworm is *Pheretima aspergillum* . . . (E. Perrier), *Pheretima vulgaris* Chen, *Pheretima guillelmi* . . . (Michaelsen) or *Pheretima pectinifera* Michaelsen. In them, dry or fresh *Whitmania pigra* Whitman and *Pheretima aspergillum* (E. Perrier) are preferred.

The extract is obtained by filtration with ultrafiltration membrane or ultrafiltration column which can stay materials with molecular weight of not more than 6,000 Dalton (6,000 Dalton is preferred). For example, the extract which is obtained with common method from the raw material (leech and/or earthworm) is ultrafiltrated with the ultrafiltration membrane or ultrafiltration column, then extract of leech and/or earthworm with molecular weight of less than 5,800 Dalton.

Particularly, following steps are preferred:

(1) Raw material is cleaned with water for injection or normal saline, steeped at low temperature and filtered. Filtrate and dregs are gained respectively;

(2) Smashed dregs are mixed with filtrate which is obtained in step (1), and homogenate is obtained. The homogenate is frozen and melted repeatedly, then centrifuged, and supernate is obtained;

(3) Supernate which is obtained in step (2) is ultrafiltrated with ultrafiltration membrane or ultrafiltration column which can stay materials with molecular weight of between 10,000 100,000 Dalton, and filtrate is obtained;

(4) The filtrate which is obtained in step (3) is ultrafiltrated with ultrafiltration membrane or ultrafiltration column which can stay materials with molecular weight of not more than 6,000 Dalton (6,000 Dalton is preferred).

If it is necessary, filtration process with ultrafiltration membrane or ultrafiltration column which can stay materials with molecular weight of not more than 6,000 Dalton (6,000 Dalton is preferred) is repeated. Thermocompression process is handled before filtration if it is necessary, for instance, filtrate is handled at 105 136° C. for 10 45 minutes.

The following steps for preparation are preferred:

(1) Raw material is cleaned with water for injection or normal saline and smashed, and then homogenate is obtained. The homogenate is frozen and melted repeatedly, then centrifuged, and supernate is obtained;

(2) The supernate which is obtained in step (1) is ultrafiltrated with ultrafiltration membrane or ultrafiltration column which can stay materials with molecular weight of between 10,000 100,000 Dalton, and filtrate is obtained;

(3) The filtrate which is obtained in step (2) is handled with method of ion-exchange chromatography;

(4) The eluent which is obtained in step (3) is ultrafiltrated with ultrafiltration membrane or ultrafiltration column which can stay materials with molecular weight of not more than 6000 Dalton after/before process of desalination.

If it is necessary, filtration process with ultrafiltration membrane or ultrafiltration column which can stay materials with molecular weight of not more than 6,000 Dalton (6,000 Dalton is preferred) is repeated.

Ultrafiltration membrane or ultrafiltration column is the common kind. Such as hollow fiber ultrafiltration column of which material is polysulfone and dissection molecular weight is not more than 6,000 Dalton (6,000 Dalton is preferred). Such as hollow fiber ultrafiltration column of which dissection molecular weight is between 10,000 and 100,000 Dalton (10,000 or 50,000 is preferred).

The ion exchange column is cation exchange column or anion exchange column. Cation exchange column is one of CM-sephadex, CM-agarose, CM-cellulose, SP-sephadex, SP-agarose, SP-cellulose and etc. Anion exchange column is one of DEAE-sephadex, DEAE-agarose, DEAE-cellulose, Q-sephadex, Q-agarose, Q-cellulose and etc.

There are polypeptide, amino acid and hypoxanthine in the extract.

Raw material of leech and/or earthworm is dry or fresh. Raw material of leech and earthworm are extracted respectively, and extract of leech and extract of earthworm are obtained respectively. Or mixture of raw material of leech and earthworm is extracted, and mixture of extract leech and earthworm is obtained.

The extract is liquid or solid after dehydration and drying.

Another object of the present invention is to provide process for preparation of the extract. The process includes filtration with ultrafiltration membrane or ultrafiltration column which can stay materials with molecular weight of not more than 6,000 Dalton (6,000 Dalton is preferred). For example, raw material of leech and/or earthworm is extracted and separated with common technology, obtained extract (also is called half-finished product or midbody) is filtered with ultrafiltration membrane or ultrafiltration column which can stay materials with molecular weight of not more than 6,000 Dalton (6,000 Dalton is preferred). Extract of leech and/or earthworm with molecular weight of less than 5,800 Dalton is obtained.

The following steps of process for preparation are preferred:

(1) Raw material is cleaned with water for injection or normal saline, steeped at low temperature and filtered. Filtrate and dregs are gained respectively;

(2) Smashed dregs are mixed with filtrate which is obtained in step (1), and homogenate is obtained. The homogenate is frozen and melted repeatedly, then centrifuged, and supernate is obtained;

(3) Supernate which is obtained in step (2) is ultrafiltrated with ultrafiltration membrane or ultrafiltration column which can stay materials with molecular weight of between 10,000 100,000 Dalton, and filtrate is obtained;

(4) The filtrate which is obtained in step (3) is ultrafiltrated with ultrafiltration membrane or ultrafiltration column which can stay materials with molecular weight of not more than 6,000 Dalton (6,000 Dalton is preferred).

If it is necessary, filtration process with ultrafiltration membrane or ultrafiltration column which can stay materials with molecular weight of not more than 206,000 Dalton (6,000 Dalton is preferred) is repeated. Thermocompression process is handled before filtration if it is necessary, for instance, filtrate is handled at 105 136° C. for 10 45 minutes.

Control is insulin human of which molecular weight is 5,800 Dalton, and materials of which molecular weight is over 5,800 Dalton are giant molecule substance.

For example, the content of giant molecule substance is determination with HPLC as follow:

A. Materials and Machines

1. Material of standard protein molecular weight: insulin human, molecular weight is 5,800 Dalton, 1 ml/ramus, purchased from the National Institute for the Control of Pharmaceutical and Biological Products.

2. Machines

Visible ultraviolet spectrophotometer (Japanese Hitachi U-3210)

High performance liquid chromatograph Water 600

High performance liquid chromatograph Agilent Hp 1100

3. Reagents

Trifluoroacetic acid, chemical pure (Science and Technology University Chemical Industry and Material Institute)

Acetonitrile, chromatographic pure (Dikma Company)

B. Chromatographic Conditions

Chromatographic column: gel chromatographic column (TSK GEL 2000 SW×1 7.8 mm*300 mm);

Mobile phase: trifluoroacetic acid-acetonitrile-water, their volume ratio is 0.025:30:70;

Ultraviolet detector: detection wave length is 214±1 nm;

Flow rate is 0.7 ml/min.

C. Determination

Suitable quantity sample and insulin human are taken accurately to be mixed with mobile phase respectively, sample solution and control solution are obtained; Sample solution and control solution are taken accurately to be injected into High performance liquid chromatograph respectively. Chromatogram is recorded. Content of materials with molecular weight of more than 5,800 Dalton is calculated by calculating content of materials corresponding to chromatographic peak of which retention time is shorter than retention time of insulin human. Content of giant molecular weight in sample is content of materials with molecular weight of more than 5,800 Dalton.

Distribution of molecular weight in extract materials is also determined with MS as follow:

Suitable quantity sample (or after desalination) is dissolved in 0.5% TFA solution. Sample solution and base material are mixed together with ratio of 1:1, targeted and tried at room temperature. The base material is DHB (2, 5-dihydroxy benzoic acid) or CCA (a-cyano-4-hydroxy cinnamic acid).

Determination machine is Autoflex (Bruker Company). MS condition (MALDI-TOF-MS); N2 lasing light emitter of which wave length is 337 nm; filate scanning (length of flying pipe is 1.6 m, accelerating voltage is 20 kv); Ion type is positive ion or negative ion.

Determination result shows that molecular weight of all components in extract of the present invention is less than 5,800 Dalton. In other words, there isn't material with molecular weight of more than 5,800 Dalton. So molecular weight of the extract for preventing or treating thrombotic diseases is not more than 5,800 Dalton.

There are polypeptide, amino acids and hypoxanthine in the extract. Polypeptide and amino acids are analyzed with suitable amino acid analyzer or High performance liquid chromatograph. For example, method of HPLC in Chinese pharmacopeia 2005 edition 1st section appendix VI D is referred to determine content of amino acid:

Chromatographic condition and systematic adaptivity test: bulking agent is octadecyl silane bonded silica gel; mobile phase is A liquid or B liquid, gradient elution, detection wave length is 338 nm and 262 nm, column temperature is 30-40° C.

A liquid: suitable quantity sodium acetate is dissolved in water for injection, and then triethylamine is added. Misce bene, PH is adjusted to neutral, and then THF is added.

B liquid: suitable quantity sodium acetate is dissolved in water for injection, and then PH is adjusted to neutral with acetic acid. Mixed liquid of acetonitrile and methanol (1:1) is added, misce bene.

Boric acid buffer solution of PH 10.4 is added in control of amino, and o-phthalaldehyde and 9-fluorene methyl formate derivative regeant are added. The mixture is stirred uniformly in order to react sufficiently and get o-phthalic acid-9-fluorene methyl formate amino acid which is control liquid. As sample, extract of the present invention is handled with the same method, and amino acid in extract is determined with high performance liquid chromatograph.

Method of HPLC in Chinese pharmacopeia 2005 edition 1th section appendix VID is referred to determine content of hypoxanthine. Fixed phase is octadecyl silanebonded silica gel, mobile phase is 0.1% dibasic sodium phosphate solution, and detection wave length is 254 nm. Theoretical plate number is not less than 3000 according to hypoxanthine.

In local stimulative test of rabbit, 1 ml extract solution of which concentration is 0.5 g/ml is injected into both leg musculus quadriceps of rabbit. Rabbit is put to death 48 hours later. Both leg quadriceps of rabbit is taken out and cut open. After being observed local stimulative reaction, the musculus quadriceps is put into 10% formaldehyde solution and checked up with common method of histopathology. Result: there is not congestion and necrosis in leg musculus quadriceps of rabbit with naked eyes. The value is 0 according to reaction grade in stimulative reaction, in other words, there is not evident change. It is confirmed that there isn't evident inflammatory reaction through pathology inspection. It also shows that the extract can't initiate evident local simulative reaction.

In blood vessel simulative test of rabbit, 1 g/kg the extract solution of which concentration is 0.5 g/ml is injected into ear vein of abbit 1 time/day for 3 days. Pieces of ear of injection position is fixed and checked up with common method of histopathology. Observe if there is inflammatory reaction in injected vein. Result: it is showed that there isn't denatured tissue and necrosis and repeat vein injection of the extract can't initiate evident inflammatory reaction to local veins.

In allergia test of cavia cobaya, 6 healthy cavia cobayas are separated to 2 groups in average. 0.5 ml the extract solution of which concentration is 0.5 g/ml is injected into belly cavity of all cavia cobayas respectively at the 1th, 3th and 5th day. Cavia cobayas of the first group is injected with 1 ml the extract solution at 15th day. Cavia cobayas of the second group is injected with 1 ml the extract solution at 22th day. To observe if there are phenomenons of piloerection, anhelation, sneezing, dry vomiting, coughing, gong sound, twitching, atrophy, death and etc in 15 minutes after injection. Result: after all injections are completed, all the phenomenons never appear. It shows that the extract can't initiate allergic response to cavia cobaya.

In haemolyticus test of rabbit, there isn't hemolytic crisis or erythroagglutination. It shows that the extract can't initiate hemolytic crisis.

So the extract can be used to prepare many kinds of relative praeparatum. The present invention is also related to a kind of drug combination containing the extract. The drug combination is pellet, capsule, drug granules, film agent, patch, coating, suppository, pilula, pulvis, ointment, mistura (fluid by mouth), syrups, tinct, ophthalmus praeparatum, nasal praeparatum, injection, asepsis powder for injection concentrated solution for injection or their sustained-release preparation and controlled release preparation. All the praeparatum is routine drug praeparatum, so they can be obtained with routine drug technology.

The extract or drug combination which can prevent or treat thrombotic diseases can be used to prepare drugs for preventing or treating thrombotic diseases. For example the drug can prevent and treat hyperlipemia, artherosclerosis, myocardial infarction, heartstroke, atherosclerotic infarct of brain, cerebral embolism, thrombosis of vein, lung embolism, pulmonary infarction, thromboangiitis obliterans, arteriosclerosis occlusion, disseminated inravascular coagulation (DIC), surgery complicated by thrombogenesis and thromboembolism, infarction of liver, infarction of kidney, infarction of cholecyst, infarction of mesentery, limbs gangrene, diabetes peripheral neuropathy, retina angiemphraxis or sudden deafness and so on.

The prominent advantage of the extract is: molecular weight of its all components is less than 5,800 Dalton, so it never or hardly initiate immunereaction. Comparing with present other extract of leech and/or earthworm, insolubility microparticles in the extract of the present invention are less and smaller, so the extract of the present invention is much safer. Comparing with present other extract of leech and/or earthworm, activity or therapeutical effect of the extract of the present invention is equivalent or better. The extract of the present invention can be used without dermal test, this can shorten time of saving patients and lessen suffering of patients.

These and other objectives, features, and advantages of the present invention will become apparent from the following detailed description, the accompanying drawings, and the appended claims.

DETAILED DESCRIPTION OF THE PREFERRED EMBODIMENT

Embodiment 1

Equivalent quantity of dry leech and earthworm are soaked in normal saline or water for injection so that they can be spread out adequately, then they are washed with normal saline or water for injection repeatedly and put into normal saline or water for injection of 2-4 times volume at 0-4 degree Celsius for 24 hours and filtered, and then filtrate and dregs are preserved for use.

The dregs are pounded to pieces with tissue gravity mill. The filtrate is mixed with collid mill, and then the mixture is grinded to homogenate of which diameter is less than 0.5 micron. The homogenate is frozen at −15° C. for 15 30 hours and melted at 0 4° C. Then above process is repeated at least 2 times.

The freeze thawing liquid is centrifugated and supernate is obtained. Then the supernate is filtered with ultrafiltration column which can stay materials with molecular weight of more than 50,000 Dalton. Obtained filtrate is filtered with ultrafiltration column which can stay materials with molecular weight of more than 10,000 Dalton again.

The above finally obtained filtrate is filtered with ultrafiltration column which can stay materials with molecular weight of not more than 6,000 Dalton. The filtrate is handled at 105-136° C. for 10-45 minutes and filtered with ultrafiltration column which can stay materials with molecular weight of not more than 6,000 Dalton again. Then extract liquid is obtained.

The extract liquid is dewatered and dried to solid if it is necessary.

There are polypeptide, amino acids and hypoxanthine in the extract as above method. There are not materials with molecular weight of more than 5,800 Dalton in the extract, so molecular weight of all obtained materials in the extract is less than 5,800 Dalton. Chromatographic detection result is shown in FIGS. 1 and 2.

Figure 1:
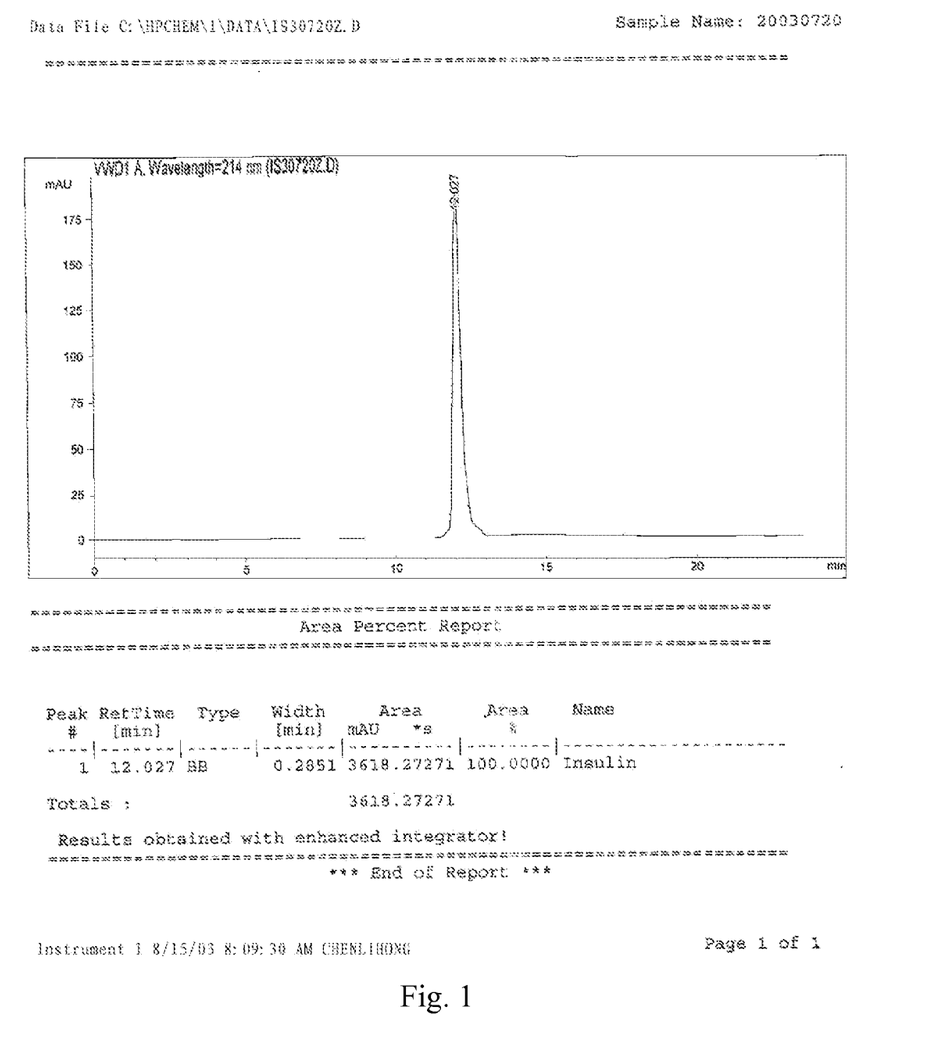
FIG. 1 is a high performance liquid chromatogram detection drawing of insulin human (5,800 Dalton).
Figure 2:
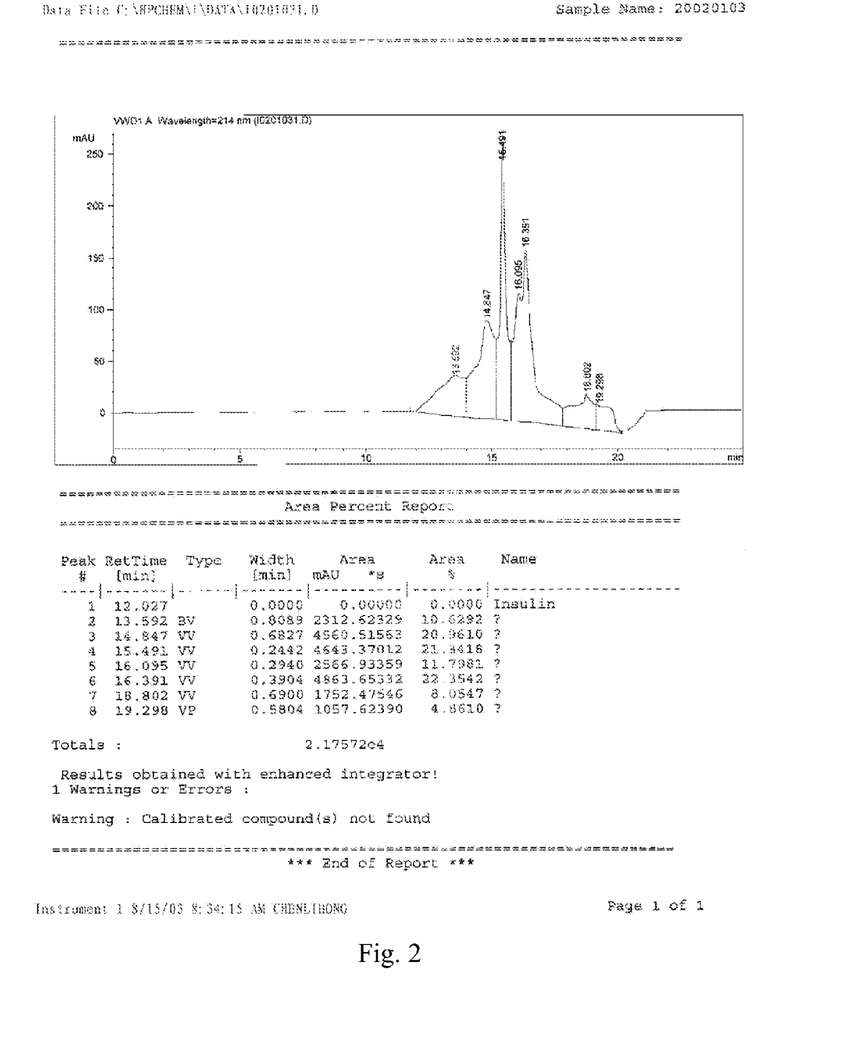
FIG. 2 is a high performance liquid chromatogram detection drawing of extract of leech and/or earthworm in the present invention.

All data in FIGS. 1 and 2 is shown in table 1 and 2.

TABLE 1 detection result of insulin human in FIG. 1

| Number of peak | Retention time (min) | Type | Width (min) | Area (mAU) | Percent of area (%) |
|---|---|---|---|---|---|
| 1 | 12.027 | BB | 0.2851 | 3618.27271 | 100 |

Total area: 3618.27271

TABLE 2 detection result of extract in the present invention in FIG. 2

| Number of peak | Retention time (min) | Type | Width (min) | Area (mAU) | Percent of area (%) |
|---|---|---|---|---|---|
| 1 | 12.027 |    | 0.0000 | 0.00000 | 0.0000 |
| 2 | 13.592 | BV | 0.8089 | 2312.62329 | 10.6292 |
| 3 | 14.847 | VV | 0.6827 | 4560.51563 | 20.9610 |
| 4 | 15.491 | VV | 0.2442 | 4643.37012 | 21.3418 |
| 5 | 16.095 | VV | 0.2940 | 2566.93359 | 11.7981 |
| 6 | 16.391 | VV | 0.3904 | 4863.65332 | 22.3542 |
| 7 | 18.802 | VV | 0.6900 | 1752.47546 | 8.0547 |
| 8 | 19.298 | VP | 0.5804 | 1057.62390 | 4.8610 |

Total area: 2.17572e4

Embodiment 2

Equivalent quantity of dry or fresh leech and earthworm are soaked in normal line or water for injection respectively so that they can be spread out adequately, then hey are washed with normal saline or water for injection repeatedly and put into normal line or water for injection of 2 4 times volume at 0 4° C. for 24 hours and filtered, then filtrate and dregs is preserved for use.

The dregs are pounded to pieces with tissue gravity mill. The filtrate is mixed with collid mill, and then the mixture is grinded to homogenate of which diameter is less than 0.5 micron. The homogenate is frozen at −15° C. for 15-30 hours and melted at 0-4° C. Then above process is repeated at least 2 times.

The freeze thawing liquid is centrifugated and supernate is obtained. Then the supernate is filtered with ultrafiltration column which can stay materials with molecular weight of more than 50,000 Dalton. Obtained filtrate is filtered with ultrafiltration column which can stay materials with molecular weight of more than 10,000 Dalton again, and filtrate is obtained.

The filtrate is adjusted to PH6.0-7.0 with buffer phosphate and washed with buffer of 5 times volume in CM-cross-link glucan cation exchange column. The eluent is collected and adjusted to PH6.0-7.0 again and washed with buffer in DEAE-cross-link glucan anion exchange column. The eluent is abandoned, and mixture of buffer of PH6.0-7.0 and 0.2-0.5 mol/L sodium chloride is added into the column to wash sequentially, the eluent is collected and is filtered with ultrafiltration column which can stay materials with molecular weight of more than 6,000 Dalton and desalted, then extract liquid is obtained. Extract of leech and extract of earthworm is obtained respectively, then they are mixed, and extract of leech and earthworm is obtained.

The extract liquid is dewatered and dried to solid if it is necessary.

There are polypeptide, amino acids and hypoxanthine in the extract as above method. There are not materials with molecular weight of not more than 5,800 Dalton in the extract, so molecular weight of all obtained materials in the extract of leech and earthworm is less than 5,800 Dalton.

Embodiment 3

Equivalent quantity of dry or fresh leech and earthworm are soaked in normal saline or water for injection respectively so that they can be spread out adequately, then they are washed with normal saline or water for injection repeatedly and put into normal saline or water for injection of 2-4 times volume at 0-4° C. for 24 hours and filtered, then filtrate and dregs is preserved for use.

The dregs are pounded to pieces with tissue gravity mill. The filtrate is mixed with collid mill, and then the mixture is grinded to homogenate of which diameter is less than 0.5 micron. The homogenate is frozen at −15° C. for 15-30 hours and melted at 0-4° C. Then above process is repeated at least 2 times.

The freeze thawing liquid is centrifugated and supernate is obtained. Then the supernate is filtered with ultrafiltration column which can stay materials with molecular weight of more than 50,000 Dalton. Obtained filtrate is filtered with ultrafiltration column which can stay materials with molecular weight of more than 10,000 Dalton again, and filtrate is obtained.

The above finally obtained filtrate is filtered with ultrafiltration column which can stay materials with molecular weight of not more than 6,000 Dalton. The filtrate is handled at 105-136° C. for 10-45 minutes and filtered with ultrafiltration column which can stay materials with molecular weight of not more than 6,000 Dalton again. Then extract liquid is obtained. And extract of leech and extract of earthworm is obtained respectively.

Figure 3:
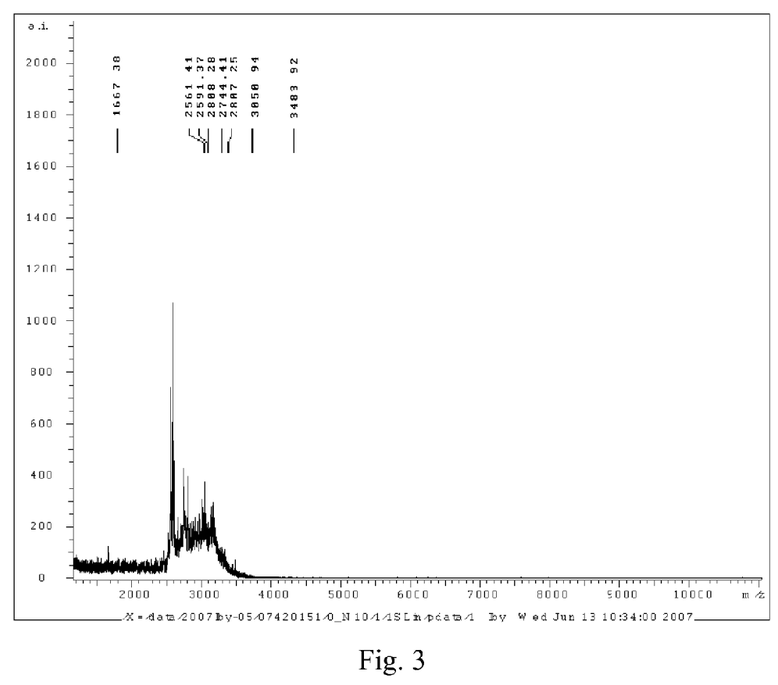
FIG. 3 is a mass spectrometric detection drawing of extract of leech in the present invention, wherein the base material is CCA, and the detection is positive ion.
Figure 4:
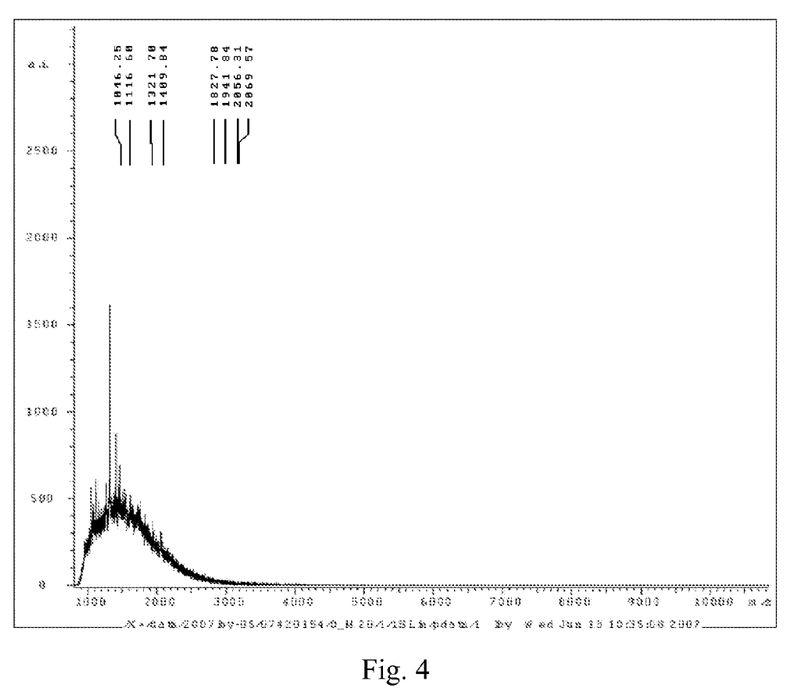
FIG. 4 is a mass spectrometric detection drawing of extract of earthworm in the present invention, the base material is DHB, and the detection is negative ion.

Molecular weight of materials in extract of leech and extract of earthworm is less than 5,800 Dalton with above method of MS. The figure is shown in FIGS. 3 and 4.

Extract of leech and earthworm is obtained after the two extract are mixed. The mixed extract is added with mannitol and 0.5-1 absorbite in order to eliminate pyrogen, then filtered with micropore film, subpackaged to ampoules, freeze dried and sealed, then the extract of freeze-dry injectable powder is obtained.

Embodiment 4

Equivalent quantity of dry leech and earthworm are soaked in normal saline or water for injection so that they can be spread out adequately, then they are washed with normal saline or water for injection repeatedly and put into normal saline or water for injection of 2-4 times volume at 0-4° C. for 24 hours and filtered, then filtrate and dregs is preserved for use.

The dregs are pounded to pieces with tissue gravity mill. The filtrate is mixed with collid mill, and then the mixture is grinded to homogenate of which diameter is less than 0.5 micron. The homogenate is frozen at −15° C. for 15-30 hours and melted at 0-4° C. Then above process is repeated at least 2 times.

The freeze thawing liquid is centrifugated and supernate is obtained. Then the supernate is filtered with ultrafiltration column which can stay materials with molecular weight of more than 50,000 Dalton. Obtained filtrate is filtered with ultrafiltration column which can stay materials with molecular weight of more than 10,000 Dalton again.

The above finally obtained filtrate is handled at 105-136° C. for 10-45 minutes and filtered with ultrafiltration column which can stay materials with molecular weight of not more than 6,000 Dalton 2-3 times. Then extract liquid is obtained.

The liquid is added with 5.4% β-cyclodextrin, stirred uniformly, soaked at 45° C. for 30 minutes and spray dried. And dry powder is obtained.

The dry powder is added with 1.5% silicon dioxide, 0.3% PVP and 1% hydroxymethylstarch. The mixture is stirred uniformly, granulated and stuffed in hard capsules. And every capsule contains 1 g the dry powder.

Embodiment 5

The extract is contained with method in embodiment 1.

The extract is added with 6.4% starch, stirred uniformly, dried and sieved. And powder for drug use is contained.

The powder is added with 0.1% gum acacia and 0.1% magnesium stearate, stirred uniformly and stuffed into hard capsules.

Embodiment 6

Influence to Clotting Time of Mouse

20±2 g male mice of Kunming species are separated to 3 groups at random, 16 mice/group. The three group of mice are injected with 10 ml/kg normal saline, 2.5 g/kg extract of ZL03148281.3 and 2.5 g/kg the extract of present invention (embodiment 1) respectively. To take blood in eye sockets of mice 15 minutes later and measure clotting time with method of micrangium. The result is shown in table 3.

TABLE 3 influence to clotting time of mouse ($\bar{\chi} \pm s$)

| Group | n | Dosage(g/kg) | Clotting time(s) | Extension of clotting time |
|---|---|---|---|---|
| Normal saline | 16 | 10.0 | 70.9 ± 17.9 | |
| Extract of ZL03148281.3 | 16 | 2.5 | 110.5 ± 31.9* | 55.8 |
| Extract of present invention | 16 | 2.5 | 113.7 ± 27.9*# | 60.4 |

Ps: *P < 0.01 comparing with normal saline group;
P > 0.05 comparing with 5extract of ZL03148281.3

The result is shown in table 3: extract of ZL03148281.3 can prolong clotting time of mice markedly (Q=5.9637 comparing with normal saline group, P<001), extract of present invention also can prolong clotting time of mice markedly (Q=6.4456 comparing with normal saline group, P<001). These two extract can both prolong clotting time of mice markedly, but there isn't distinguished difference between them (Q=0.4819, P>0.05).

Embodiment 7

Influence to Platelet and Platelet Sticking Rate of Rat

1. Influence to Platelet 220 270 g male rats is separated to 3 groups, 10 rats/groups. The three groups of mice are injected with 5 ml/kg normal saline, 1.0 g/kg the extract of present invention and 1.0 g/kg extract of ZL03148281.3 respectively. To take blood in eye sockets of mice 15 minutes later and measure platelet with globulimeter. The result is shown in table 4.

2. Influence to Platelet Sticking Rate 220 270 g male rats is separated to 3 groups, 10 rats/groups. The three groups of mice are injected with 5 ml/kg normal saline, 1.0 g/kg the extract of present invention and 1.0 g/kg extract of ZL03148281.3 respectively. To take blood in eye sockets of mice 15 minutes later and measure platelet this is number of platelet before sticking. 1.5 ml blood is put into tube in which there is 0.3 ml 3.8% natrium citricum solution. To stirred uniformly and take 1 ml mixture into a silicon tube ring. The ring is put into vitro thrombogenesis platelet adhesion reaction machine and run for 5 minutes with speed of 17 turns/minute. To take blood to measure number of platelet as number of platelet after sticking and calculate platelet sticking rate. The result is shown in table 4. Calculation method of platelet is as following:

sticking rate(%)=number of platelet before sticking number of platelet after sticking/number of platelet before sticking×100%

TABLE 4 influence to platelet and platelet sticking rate of rat

| group | n | Dosage (g/kg) | Platelet number ($10^3/mm^3$) | Reduction of platelet (%) | platelet sticking rate (%) |
|---|---|---|---|---|---|
| Normal saline | 10 | 5.0 | 171.1 ± 45.6 | | |
| Extract of ZL03148281.3 | 10 | 1.0 | 148.5 ± 22.1* | 12.2 | 37.5 ± 13.5 |
| Extract of present invention | 10 | 1.0 | 131.4 ± 17.2**# | 15.2 | 32.0 ± 12.9# |

Ps: *P < 0.05,
**P < 0.01 comparing with normal saline group;
P > 0.05 comparing with extract of ZL03148281.3

The result is shown in table 4: extract of ZL03148281.3 can lower platelet number of normal rats markedly (Q=2.9260, P<0.05 comparing with normal saline group, P<0.01), extract of present invention also can lower platelet number of normal rats markedly (Q=5.1399, P<0.01 comparing with normal saline group, P<0.01). These two extract can both lower platelet number of normal rats, but there isn't distinguished difference between them (Q=2.2139, P>0.05). It is shown that extract of present invention and extract of ZL03148281.3 can both lower platelet number and platelet sticking rate and decrease formation of thrombus.

Embodiment 8

Detection of Visible Extraneous Material and Insoluble Microparticle

Extract of leech and earthworm (called extract of ZL03148281.3) is obtained with dry leech and dry earthworm referring to method in ZL03148281.3.

1 detection of visible extraneous material: visible extraneous materials in extract of present invention (embodiment 1) and extract of ZL03148281.3 are detected respectively referring to Chinese Pharmacopeia (2005 edition) praeparatum general notice injection rule. The result is shown in table 5.

TABLE 5 detection result of visible extraneous material

| Item sample | Qualified rate of lamp detection | Short and small fiber |
| --- | --- | --- |
| extract of present invention | 92.7 | 3.9 |
| extract of ZL03148281.3 | 63.7 | 28.5 |

The result shows that there is novel difference between extract of present invention and extract of ZL03148281.3 in visible extraneous material. Qualified rate of lamp detection and short and small fiber of extract of present invention are better than these of extract of ZL03148281.3. So extract of present invention is safer.

2 detection of insoluble microparticle: insoluble microparticle in extract of present invention (embodiment 1) and extract of ZL03148281.3 are detected respectively referring to Chinese Pharmacopeia (2005 edition) praeparatum general notice injection rule. The result is shown in table 6.

TABLE 6 detection result of insoluble microparticle

| Item sample | Microparticle of more than 10 um (average value/ramus) | Microparticle of more than 25 um (average value/ramus) |
| --- | --- | --- |
| extract of present invention | 196/ramus | 65/ramus |
| extract of ZL03148281.3 | 250/ramus | 110/ramus |

The result shows that there is novel difference between extract of present invention and extract of ZL03148281.3 in insoluble microparticle. Insoluble microparticle number of extract of present invention is much less than that of extract of ZL03148281.3. So extract of present invention is safer.

Above results shows that: there isn't evident difference in drug action between extract of present invention and extract of ZL03148281.3, and the former is better than the latter in some indexes. In other words, extract of present is much safer with same drug activity.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of obtaining an extract, comprising the steps of:
   (1) cleaning raw material comprising leech and earthworm with water, and then steeping and smashing said raw material for forming homogenate;
   (2) repeatedly freezing and melting said homogenate, then centrifuging for obtaining supernate;
   (3) ultrafiltratinq said supernate with an ultrafiltration device of molecular weight exclusion limit of 10,000-100,000 Daltons for obtaining a first filtrate;
   (4) thermocopressinq said first filtrate at 105-136° C. for 10-45 minutes;
   (5) ultrafiltrating said filtrate with an ultrafiltration device of molecular weight exclusion limit of less than 6000 Daltons for obtaining a second filtrate; and
   (6) obtaining from said second filtrate an extract having a molecular weight less than 5800 Daltons.

2. The method of obtaining an extract, as according to claim 1, wherein said raw material is dry.

3. The method of obtaining an extract, as according to claim 1, wherein said raw material is fresh.

4. The method of obtaining an extract, as according to claim 1, further comprising drying said extract.

* * * * *